United States Patent [19]

Ma et al.

[11] Patent Number: 6,054,584

[45] Date of Patent: *Apr. 25, 2000

[54] PROCESS FOR EXTRACTING AND PURIFYING MORPHINE FROM OPIUM

[75] Inventors: Junning Ma, North Wales, Pa.; Robert C. Corcoran, Laramie, Wyo.

[73] Assignee: The Board of Regents of the University and Community College System of Neveda, Reno, Nev.

[ * ] Notice: This patent issued on a continued prosecution application filed under 37 CFR 1.53(d), and is subject to the twenty year patent term provisions of 35 U.S.C. 154(a)(2).

[21] Appl. No.: 08/753,061

[22] Filed: Nov. 19, 1996

Related U.S. Application Data

[60] Provisional application No. 60/007,418, Nov. 21, 1995.

[51] Int. Cl.$^7$ .................................................. C07D 489/00
[52] U.S. Cl. .................................................. 546/44
[58] Field of Search ................................................. 546/44

[56] References Cited

U.S. PATENT DOCUMENTS

| 1,048,712 | 12/1912 | Lloyd | 546/44 |
| 2,715,627 | 8/1955 | Mehltretter et al. | 546/44 |

FOREIGN PATENT DOCUMENTS

| 189439 | 1/1966 | Russian Federation | 546/44 |
| 1 80 189 | 10/1935 | Switzerland | 546/44 |
| 457 433 | 11/1936 | United Kingdom | 546/44 |
| 750359 | 6/1956 | United Kingdom | 546/44 |

OTHER PUBLICATIONS

Loeffler. Chem Abstr vol. 62, Entry 11640 b abstr. DD 28733, 1965.

Trojanek, Chem Abstr vol. 98 Entry 81d0 abstr Czech 197403, 1982.

Bentley Chemistry of the Morphine Alkaloids, Oxford, Clarendon Press, p. 16, 1954.

*Primary Examiner*—Mukund J. Shah
*Assistant Examiner*—Pavanaram K Sripada
*Attorney, Agent, or Firm*—Morgan, Lewis & Bockius LLP

[57] ABSTRACT

A process for extracting morphine from opium is described. In the process, opium is extracted with a basic alcoholic solution. The basic alcoholic solution is filtered and the alcohol removed from the filtrate to leave a residue. The residue is then extracted with a basic aqueous solution having a pH of at least 11. The basic aqueous solution may be filtered to remove any solid matter remaining after the aqueous extraction step, and then be stirred with a sufficient amount of a salt to avoid emulsion formation. The basic aqueous solution or filtrate is then extracted with benzene or toluene. Next, adjusting the pH of the basic aqueous filtrate to pH 8.5 to 9.5 allows the morphine to precipitate and be recovered.

7 Claims, 1 Drawing Sheet

MORPHINE PURIFICATION PROCESS

PROCESS FOR EXTRACTING AND PURIFYING MORPHINE FROM OPIUM

This application claims the benefit of the filing date of U.S. provisional application Serial No. 60/007,418 filed Nov. 21, 1995.

FIELD OF THE INVENTION

This invention relates to an improved process for the extraction and purification of morphine from opium. The object of this invention is to provide a more economical method of preparing morphine that utilizes less environmentally toxic solvents.

BACKGROUND

Morphine is useful as an analgesic drug. It is also used as the starting material for the preparation of codeine, which is another analgesic and antitussive drug. Morphine occurs naturally in opium to the extent of 9 to 17% by weight, depending upon the opium source.

There are many alternative methods of extracting and purifying morphine from opium. However, these methods suffer from several disadvantages, such as prolonged extraction times, low efficiencies and the involvement of hazardous chemicals such as chloroform and sulfur dioxide. What is needed is a cost-effective process which does not require large amounts of potentially toxic or hazardous solvents. When viewed from this perspective, none of the current methods are entirely satisfactory.

Generally, current methods extract the alkaloids present in opium with either water or an acidic (e.g. oxalic acid) solution. Due to the limited solubility of the alkaloids in aqueous solutions, the extract is very dilute. This results in a large amount of the aqueous extract. Recovery of the alkaloids from the aqueous extract also requires large amount of organic solvents. The process is also lengthy and labor intensive. One batch of opium generally needs to be extracted four times over a period of four days for complete recovery of the alkaloids. Separation and purification of morphine from the other alkaloids in the aqueous extract is also time consuming and relatively complicated due to the physical properties of the extract and the nature of the substances present.

SUMMARY OF THE INVENTION

The present invention relates to a process for extracting morphine from opium. The process of the invention answers the deficiencies of prior art processes. In the process, opium is extracted with a basic alcoholic solution. The basic alcoholic solution is filtered and the alcohol removed from the filtrate to leave a residue. The residue is then extracted with a basic aqueous solution having a pH of at least 11. The basic aqueous solution may be filtered to remove any solid matter remaining after the aqueous extraction step, and may then be stirred with a sufficient amount of a salt to avoid emulsion formation. The basic aqueous solution is then extracted with a substantially water-immiscible solvent such as benzene or toluene. Next, adjusting the pH of the basic aqueous solution to pH 8.5 to 9.5 allows the morphine to precipitate and be recovered.

DESCRIPTION OF THE INVENTION

Figure 1:
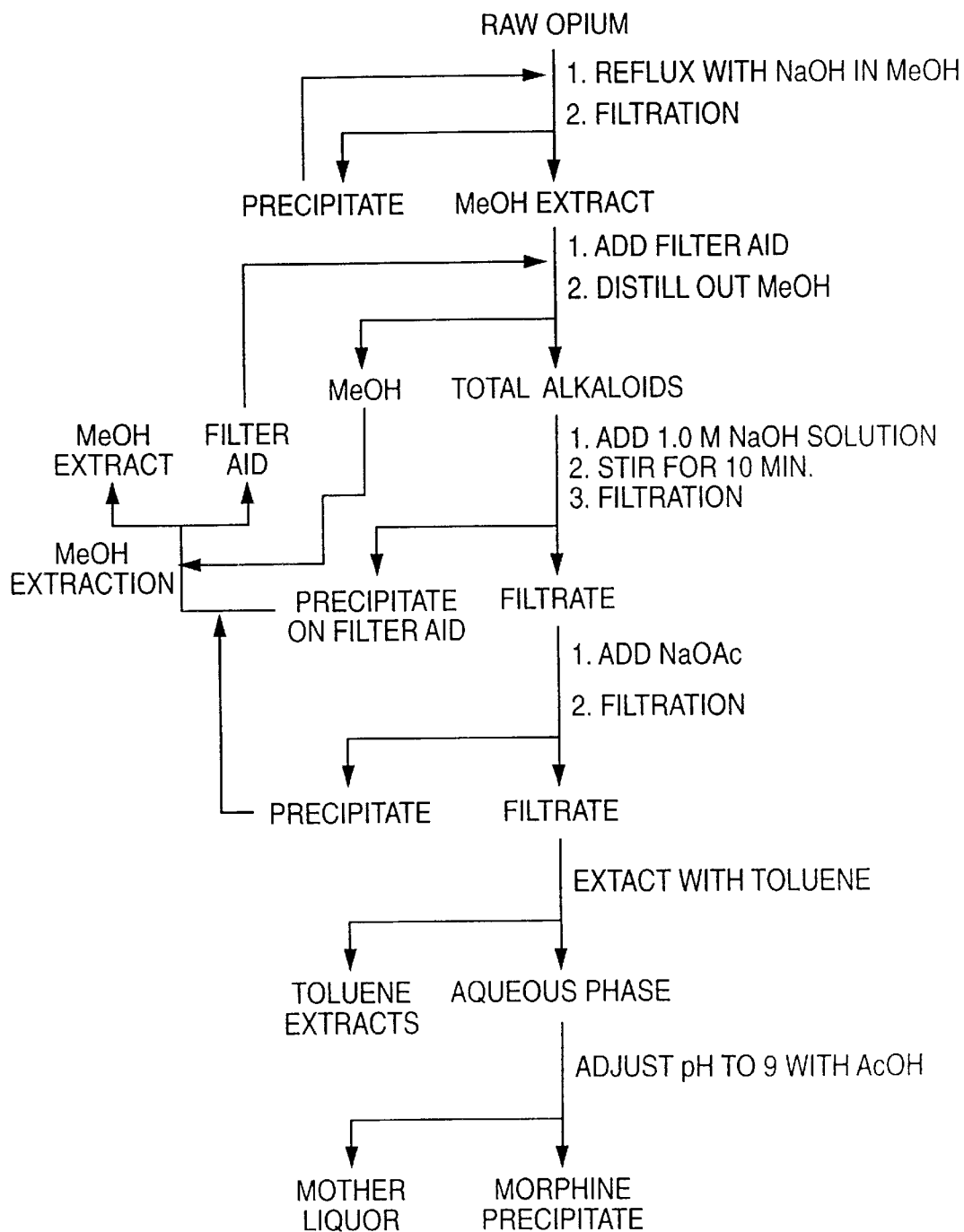
FIG. 1 depicts a preferred process according to the invention for extracting and purifying morphine from opium.

According to the invention described herein, morphine is extracted from opium by stirring and/or heating, or preferably refluxing, opium in a basic solution of an alcohol, preferably methanol at about pH 9. The pH may be adjusted by the addition of an inorganic base (alkali hydroxide, or carbonate), ammonia, and the like. Preferred inorganic bases include, but are not limited to, sodium hydroxide and potassium hydroxide. After the extraction is complete, the alcohol extract is filtered to remove the undissolved particulate matter. The alcohol itself is then removed from the extracted alkaloids, preferably by evaporation under reduced pressure. The resulting residue, which contains the alkaloids, is mixed or extracted with an basic aqueous solution having a pH of at least 11, preferably an aqueous solution of an alkali hydroxide. This converts the morphine free base present into its anionic (morphinate) form which is soluble in basic solutions at pH values of 11 or above. Other opium alkaloids are relatively insoluble and, in general, at least partially precipitate out of the basic aqueous solution. After removing any precipitate, preferably by filtration, the remaining alkaloids are separated from the morphine-containing basic aqueous solution by extraction with a substantially water-immiscible solvent, such as toluene or benzene. Finally, the morphine free base is precipitated out of the resulting aqueous solution by adjusting the pH of the aqueous filtrate to pH 8.5 to 9.5. Preferably, the pH to precipitate the morphine ranges from about 9 to 9.3, and most preferably is about 9.1. This is accomplished by adding either an organic acid or a mineral acid. The yield and purity of morphine produced by this procedure are economically satisfactory. The morphine obtained from this process may then be further purified by known methods or utilized directly in a further process to convert it into codeine.

As discussed above, the extraction of morphine from opium may be accomplished by stirring and/or heating, preferably refluxing, opium with a basic solution of an alcohol capable dissolving morphine in its neutral, cationic, and/or anionic form. Preferably, the alcohol is a $C_1$–$C_6$ alcohol. Particularly preferred alcohols include methanol, ethanol, and isopropanol. Mixtures of alcohols may also be used. Methanol, the preferred solvent for the invention, is a excellent solvent for extracting alkaloids from opium. Almost all of the alkaloids, especially morphine, are highly soluble in methanol. Advantageously, the alkaloids are soluble in methanol in their neutral, cationic, or anionic forms. The addition of an alkali, alkaline earth, or other suitable base to adjust the pH of the alcohol, to about 9, makes the extraction process more efficient. This results in more alkaloids and less impurities being extracted into the alcohol. Refluxing opium in a basic solution of the alcohol, preferably methanol at about pH 9, for approximately one to two hours extracts more than 90% of the morphine present. In a preferred embodiment, 5 g of opium, cut into small pieces, may be extracted by reflux with 0.2 to 0.6 g, preferably 0.4 g, of sodium hydroxide in 25 ml of methanol for 1 to 2 hrs.

An additional extraction of the opium with a basic alcohol, such as methanol at pH 9, can recover essentially all of the alkaloids from opium. The second extract can either be combined with the first extract or can be used to extract another batch of opium. Separation of the alcohol extract from the undissolved residue by filtration or other similar means is generally easy and fast. Unlike an aqueous extraction process, the assistance of filter aid at this step is generally unnecessary.

The removal of alcohol by distillation, under reduced pressure, at elevated temperatures, or by other known techniques is much easier and more rapid than the concentration of aqueous extracts or organic solutions (e.g. toluene) usually required in prior art methods. A small amount of filter aid may be added to the alcohol extract before distillation to prevent the alcohol extract from foaming and bumping. As another advantage, the recovered alcohol, particularly methanol, can be recycled and used for another extraction without further purification.

In the prior art extraction methods, morphine is usually kept as an acid salt due to concerns regarding the stability of morphine in basic solutions. To test the stability of morphinate in basic aqueous solutions, morphinate was analyzed by High Performance Liquid Chromatography (HPLC) and then allowed to stay overnight at room temperature. The morphinate was then reanalyzed by HPLC. No loss of morphine was found.

According to the invention, the residue remaining after removing the alcohol is then extracted with a basic aqueous solution having a pH of at least 11. Preferably, the basic aqueous solution is a solution of an alkali hydroxide such as sodium hydroxide or potassium hydroxide. Solutions of other bases may also be used. Maintaining the pH of the aqueous extract at this pH and preferably within a relatively narrow preferred range allows high quality morphine to be obtained with good recovery. At lower pH values, greater amounts of morphine may be lost in the initial precipitate. At higher pH values, less impurities may be extracted into toluene. Maintaining the pH in the range of 11.5 to 11.9 is, therefore, preferred.

The basic aqueous solution may optionally be filtered to remove any solid material remaining after the aqueous extraction step. Filtering the basic aqueous solution at this point removes insoluble non-morphine alkaloids. Any precipitate may be washed with an additional quantity of the basic aqueous solution to ensure increased recovery of the morphine.

The basic aqueous solution or filtrate, if filtered, is then extracted with a substantially water-immiscible organic solvent to remove the remaining alkaloids from the basic aqueous filtrate. Suitable solvents include, but are not limited to, benzene, toluene, xylene, diethyl ether, and chloroform. Separation of the resulting aqueous and organic phases may be accomplished by techniques known in the art.

Theoretically, non-morphine alkaloids are supposed to precipitate out of concentrated aqueous solutions at pH values around 11–12. However, the presence of concentrated morphinate ions may increase the solubility of the other alkaloids. Thus, substantial amounts of non-morphine alkaloids may remain in solution. Direct extraction of the basic aqueous solution or filtrate, if filtered, with a substantially water-immiscible solvent can remove those alkaloids, but may result in formation of an emulsion. To avoid emulsion formation, the aqueous solution/filtrate may, before extraction with the substantially water-immiscible solvent, first be treated with a sufficient amount of an alkali metal salt or alkaline earth metal salt, for example 0.5 to 5 grams salt for each 5 grams of opium. Preferred salts are, for example, lithium chloride, lithium bromide, lithium acetate, sodium chloride, sodium bromide, sodium acetate, potassium chloride, potassium bromide, or potassium acetate. A preferred amount of the salt is 0.5 to 2 grams per 5 grams of opium. Sodium chloride and sodium acetate are preferred salts with sodium acetate being particularly preferred. The extract may then preferably filtered again to get rid of any gummy or other precipitate prior to extracting with a substantially water-immiscible solvent, such as benzene or toluene.

The sequence of the morphine purification procedure may, however, affect the recovery of morphine. For example, if, to avoid emulsion formation upon extraction, a salt is added to the basic aqueous solution before it is filtered after the aqueous extraction step, as much as about 20% of the morphine may precipitate out along with the other alkaloids. Accordingly, the recovery of morphine will be substantially lower.

When extracting the aqueous solution/filtrate with a substantially water-immiscible solvent, such as toluene or benzene, a small amount, generally about 8%, of the morphine may be extracted into the solvent. This may be recovered by back extraction with additional basic solution, for instance, a sodium hydroxide solution. Any loss of morphine in the aqueous mother liquor, about 2%, may be recovered by additional extraction with the solvent. For health reasons, the use of toluene is preferred, particularly over benzene, in the process of the invention.

Any alkaloids precipitated on a filter aid or paper in the process may be recovered by extraction with an alcohol, preferably methanol. The filter aid can be used again without further purification. The other opiate alkaloids that were extracted into the substantially water-immiscible solvent may be combined with the alkaloids which precipitated from the aqueous extract at pH 11.5 to 11.9 and further purified by other known methods.

After extraction with the substantially water-immiscible solvent, the pH of the basic aqueous solution/filtrate is adjusted to about 8.5 to 9.5 to precipitate the morphine. Preferably, the pH is adjusted to 9 to 9.3 and more preferably to 9.1. The pH may be adjusted using an acid such as, for example, sulfuric acid, hydrochloric acid or acetic acid. Preferably, a 50% acetic acid in water solution is used.

The precipitated morphine may then be recovered using techniques known in the art such as filtration or decantation. The recovered morphine is preferably washed with water before drying.

The foregoing procedure provides a cost-effective process for isolating morphine from opium. This procedure provides good recovery and a high quality product FIG. 1 depicts a preferred process of the invention. The whole process, from extraction of opium to precipitation of purified morphine, can generally be completed in one day. This is much more efficient than other existing commercial purification methods.

The following specific example illustrates the invention, but is not intended to limit the scope of the invention.

EXAMPLE 5 g of opium were cut into small pieces and extracted by reflux with 0.4 g of sodium hydroxide in 25 ml of methanol for 1 to 2 hrs. The methanol extract was then filtered to remove particulate materials. After addition of 1 g of filter aid to the methanol extract, which contained 465 to 485 mg of morphine, the methanol was removed under reduced pressure. The residue was then mixed with 5.5 ml of 1.0 N sodium hydroxide solution at 35° C. for 10 min. and the pH adjusted to about 11.5 to 11.9 with 50% acetic acid in water. This aqueous extract was then filtered and the precipitate washed with 5.5 ml of 0.01 N sodium hydroxide solution. The combined aqueous filtrate was stirred with 0.5 g of sodium acetate for 10 minutes and filtered again. The filtrate was then extracted twice with 5 ml of toluene and the pH of the aqueous filtrate was then adjusted to pH 9.1, with 50% acetic acid in water. The mixture was allowed to remain for a period of 6–10 hrs at room temperature for complete precipitation and was then filtered. This precipitate was washed with water and dried at room temperature. This final precipitate contained 400–426 mg of morphine, which represented a recovery of 86–88% based upon the amount of morphine in the initial methanol extract. The purity of morphine following this procedure was 84% to 86% by weight.

What is claimed is:

1. A process for selectively extracting morphine from opium, comprising the steps of:

extracting opium with a basic solution of a $C_1$–$C_6$ alcohol capable of dissolving morphine in its neutral, cationic, or anionic form, filtering the alcohol solution, removing the alcohol from filtrate to leave a residue, extracting the residue with a basic aqueous solution having a pH of at least 11, optionally filtering the basic aqueous solution to remove any solid matter remaining after the aqueous extraction step, optionally stirring the basic aqueous solution with a sufficient amount of a salt to avoid emulsion formation, extracting the basic aqueous solution with a substantially water-immiscible organic solvent to remove non-morphine alkaloids from the solution, adjusting the pH of the basic aqueous filtrate to pH 8.5 to 9.5 to precipitate morphine, and recovering the morphine.

2. A process of claim 1, comprising the steps of:

extracting opium by refluxing in a basic methanol solution having a pH of about 9, filtering the methanol solution to remove any particulate matter remaining from the methanol extraction, removing the methanol from filtrate to leave a residue, extracting the residue with an aqueous solution of alkali hydroxide having a pH of at least 11, optionally filtering the basic aqueous solution to remove any solid matter remaining after the aqueous extraction step, optionally stirring the basic aqueous solution with a sufficient amount of a salt selected from lithium chloride, lithium bromide, lithium acetate, sodium chloride, sodium bromide, sodium acetate, potassium chloride, potassium bromide, and potassium acetate, to avoid emulsion formation, extracting the basic aqueous solution with a substantially water-immiscible organic solvent selected from benzene, toluene, xylene, diethyl ether, chloroform, and mixtures thereof, to remove non-morphine alkaloids from the solution, adjusting the pH of the basic aqueous filtrate to pH 8.5 to 9.5 to precipitate morphine, and recovering the morphine.

optionally filtering the basic aqueous solution to remove any solid matter remaining after the aqueous extraction step, optionally stirring the basic aqueous solution with a sufficient amount of a salt selected from lithium chloride, lithium bromide, lithium acetate, sodium chloride, sodium bromide, sodium acetate, potassium chloride, potassium bromide, and potassium acetate, to avoid emulsion formation, extracting the basic aqueous solution with a substantially water-immiscible organic solvent selected from benzene, toluene, xylene, diethyl ether, chloroform, and mixtures thereof adjusting the pH of the basic aqueous filtrate to pH 8.5 to 9.5 to precipitate morphine, and recovering the morphine.

3. A process of claim 2, further comprising, before the extraction step of extracting with a substantially water-immiscible organic solvent, the steps of:

filtering the basic aqueous solution to remove any solid material remaining after the aqueous extraction step, stirring the basic aqueous solution with a sufficient amount of sodium acetate to avoid emulsion formation; and filtering the resulting solution.

4. A process of claim 2 further comprising, after filtering the methanol solution, the steps of:

extracting the particulate material a second time by refluxing in a second basic methanol solution having a pH of about 9, filtering the second methanol solution to remove any particulate matter remaining from the methanol extraction, and combining the second methanol filtrate with the first methanol filtrate for use in the methanol removal step.

5. A process of claim 1, wherein extracting step refluxes opium in a basic solution of an alcohol selected from methanol, ethanol, isopropanol, and mixtures thereof, and having a pH of about 9; and wherein the substantially water immiscible solvent is selected from benzene, toluene, xylene, diethyl ether, chloroform, and mixtures thereof.

6. A process of claim 5 further comprising, after filtering the methanol solution, the steps of:

extracting the particulate material a second time by refluxing in a second basic alcohol solution having a pH of about 9, filtering the basic second alcohol solution to remove any particulate matter remaining from the alcohol extraction, and combining the second basic alcohol filtrate with the first alcohol filtrate for use in the alcohol removal step.

7. A process for selectively extracting morphine from opium, comprising the steps of:

extracting opium with a basic solution of methanol, filtering the methanol solution, removing the methanol from filtrate to leave a residue, extracting the residue with a basic aqueous solution having a pH of at least 11, optionally filtering the basic aqueous solution to remove any solid matter remaining after the aqueous extraction step, optionally stirring the basic aqueous solution with a sufficient amount of a salt to avoid emulsion formation, extracting the basic aqueous solution with a substantially water-immiscible organic solvent to remove non-morphine alkaloids from the solution, adjusting the pH of the basic aqueous filtrate to pH 8.5 to 9.5 to precipitate morphine, and recovering the morphine.

* * * * *